(12) United States Patent
Zeng et al.

(10) Patent No.: US 11,331,185 B2
(45) Date of Patent: May 17, 2022

(54) DELIVERY SYSTEM FACILITATING RETRIEVAL OF INTERVENTIONAL DEVICE

(71) Applicant: VENUS MEDTECH (HANGZHOU), INC., Zhejiang (CN)

(72) Inventors: Min Frank Zeng, Irvine, CA (US); Zhenjun Zi, Hangzhou (CN)

(73) Assignee: Venus Medtech (Hongzhou) Inc, Hongzhou (CN)

( * ) Notice: Subject to any disclaimer, the term of this patent is extended or adjusted under 35 U.S.C. 154(b) by 552 days.

(21) Appl. No.: 16/361,561

(22) Filed: Mar. 22, 2019

(65) Prior Publication Data

US 2019/0269510 A1 Sep. 5, 2019

Related U.S. Application Data

(63) Continuation of application No. PCT/CN2017/102211, filed on Sep. 19, 2017.

(51) Int. Cl.
*A61F 2/24* (2006.01)
*A61F 2/95* (2013.01)

(52) U.S. Cl.
CPC .......... *A61F 2/2436* (2013.01); *A61F 2/9517* (2020.05); *A61F 2002/9528* (2013.01)

(58) Field of Classification Search
CPC .... A61F 2/2436; A61F 2/9517; A61F 2/9522; A61F 2/95; A61F 2002/9528;
(Continued)

(56) References Cited

U.S. PATENT DOCUMENTS

2007/0156222 A1* 7/2007 Feller ........................ A61F 2/95
 623/1.11
2010/0094392 A1* 4/2010 Nguyen ............ A61M 25/0668
 623/1.11
(Continued)

FOREIGN PATENT DOCUMENTS

CN 1745727 A 3/2006
CN 2783951 Y 5/2006
(Continued)

OTHER PUBLICATIONS

English Translation of WO-2006026912-A1 (Year: 2006).*
(Continued)

*Primary Examiner* — Diane D Yabut
*Assistant Examiner* — Christina C Lauer
(74) *Attorney, Agent, or Firm* — Raymond Sun

(57) ABSTRACT

A delivery system facilitating retrieval of interventional device includes a sheath, an operation handle for driving the sheath to move, and a tube axially slidably engaging with the pusher section. The sheath includes a carrier section at a proximal end for surrounding the interventional device and a pusher section connected with the carrier section. Depending on different axial positions, the tube assumes an initial configuration in which a proximal end portion thereof is at a periphery of the pusher section, and an operation configuration in which the proximal end portion is held tightly around the carrier section and limits further expansion of the carrier section. The delivery system functions to hold the support frame tightly by surrounding the sheath with the axially movable tube, retrieving the support frame and preventing the support frame from falling off from a core shaft, thereby reducing risks in surgery and the mortality rate. The tube may be manually driven or driven in other (Continued)

ways, which is convenient to coordinate with known control handles or sheaths.

19 Claims, 10 Drawing Sheets

(58) Field of Classification Search
CPC .... A61F 2002/9534; A61F 2/962; A61F 2/97; A61F 2002/9665; A61F 2/966
See application file for complete search history.

(56) References Cited

U.S. PATENT DOCUMENTS

| | | | |
|---|---|---|---|
| 2014/0046428 A1* | 2/2014 | Cragg | A61F 2/954 623/1.12 |
| 2014/0336742 A1 | 11/2014 | Costello | |
| 2017/0000607 A1* | 1/2017 | Crisostomo | A61F 2/95 |

FOREIGN PATENT DOCUMENTS

| | | |
|---|---|---|
| CN | 202235791 U | 5/2012 |
| CN | 105943210 A | 9/2016 |
| CN | 107080608 A | 8/2017 |
| CN | 107157621 A | 9/2017 |
| WO | WO-2006026912 A1 * 3/2006 | ........... A61F 2/2418 |

OTHER PUBLICATIONS

International Search Report dated Dec. 26, 2017 for corresponding PCT Application No. PCT/CN2017/102211.
International Written Opinion dated Feb. 22, 2018 for corresponding PCT Application No. PCT/CN2017/102211.

* cited by examiner

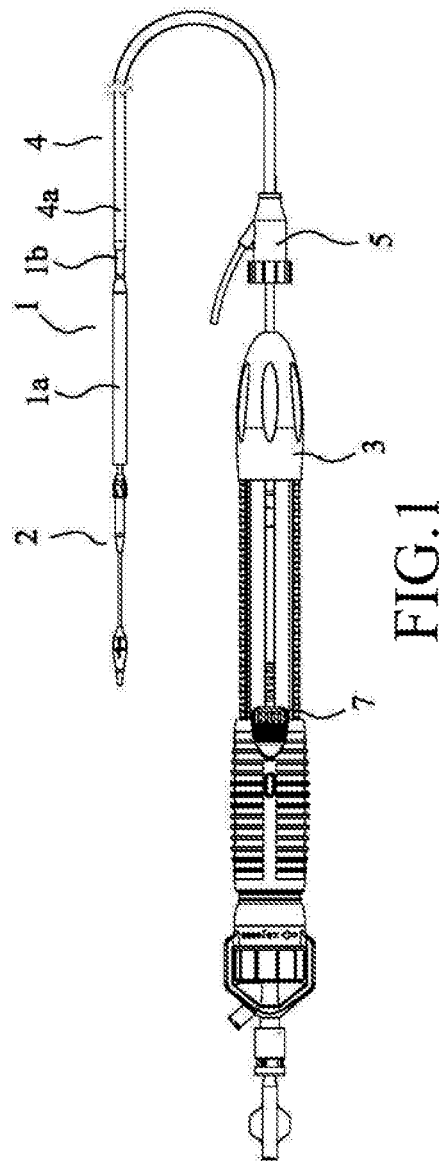
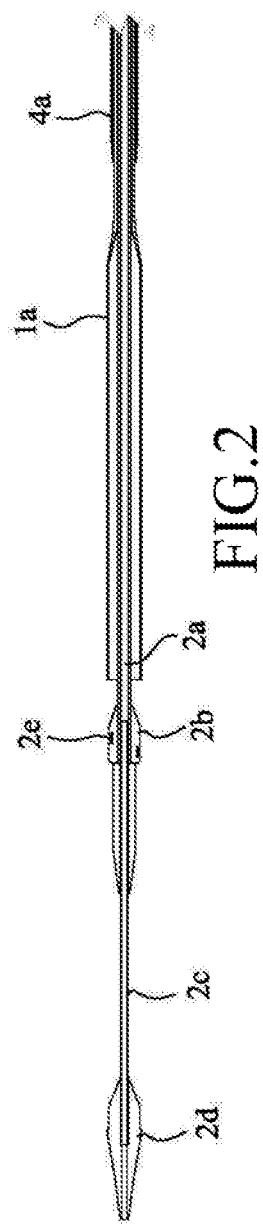
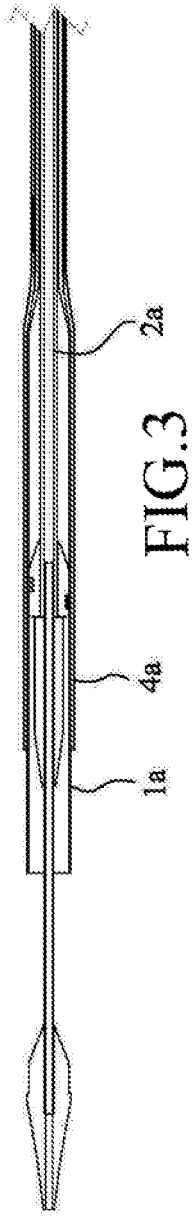

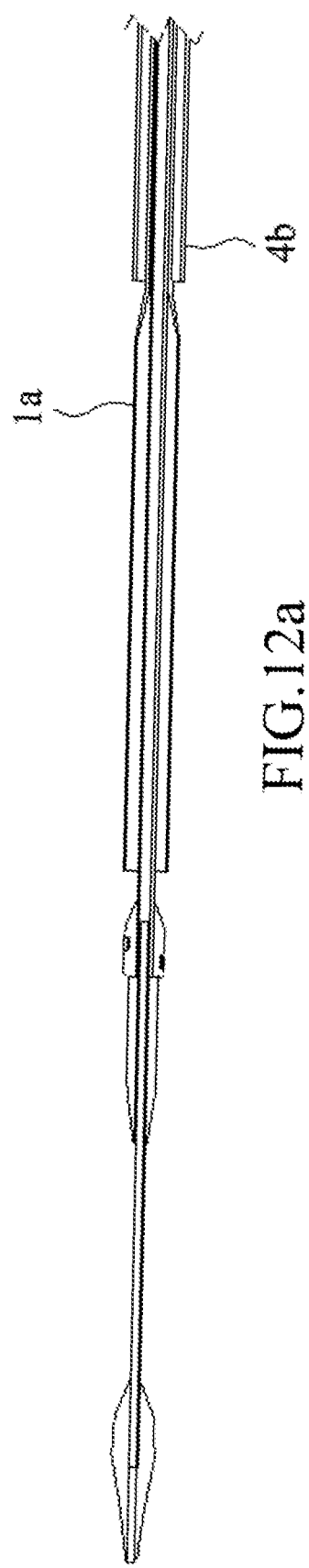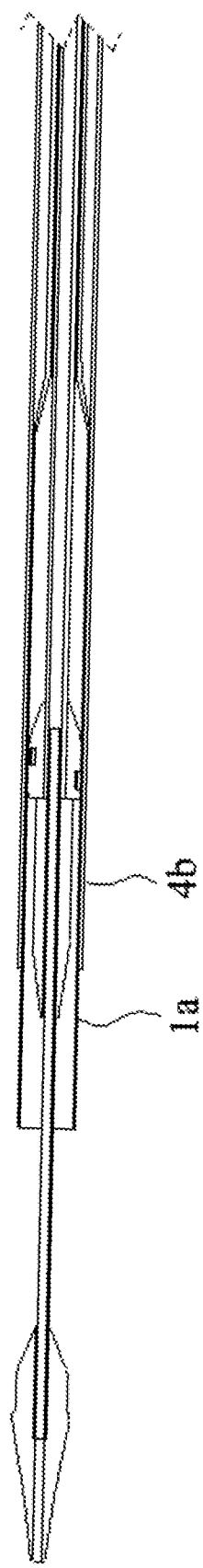
FIG.12a
FIG.12b

DELIVERY SYSTEM FACILITATING RETRIEVAL OF INTERVENTIONAL DEVICE

TECHNICAL FIELD

The present invention relates to the field of medical apparatus and instruments, and in particular to a delivery system for an interventional device.

BACKGROUND

Compared with surgical operation, interventional operation is a type of medical technology rising and developing rapidly in recent years as it involves less trauma and invasiveness than surgical operation. During an interventional operation, a specific delivery system is usually required to deliver a diagnostic instrument or an implanted device or the like to a lesion site.

A typical delivery system mainly includes a sheath, a core shaft arranged in the sheath and an operation handle. The core shaft usually has a core tube and an interventional device connecting portion which are connected in sequence along the way away from the operator. In the process of implanting the interventional device, the interventional device is first compressed and connected with the interventional device connecting portion, with the sheath mounted around the core shalt, which keeps the interventional device in the compressed profile. The sheath and the core shaft carrying the interventional device advance from an entrance of a blood vessel to the lesion site. Then, the sheath is withdrawn to release the interventional device which then expands at body temperature and positions itself in place, and finally the sheath and the core shaft is withdrawn.

Complications have become apparent with the world wide application of endovascular interventional therapy. Taking interventional aortic valve replacement and pulmonary valve replacement operations, for example, during the procedure, femoral artery puncture or femoral vein puncture is usually required, and a delivery sheath carrying a valve is delivered through the femoral artery or the femoral vein to place the valve at the aortic annulus or pulmonary annulus. In the process of releasing a support frame, however, it is difficult for an operator to guarantee the accuracy of the position of the support frame and the size of the selected valve, which leads to valve displacement, and failure to achieve the expected treatment effect, and might even cause the support frame to slide into a ventricle or block a coronary which would result in the risk of open-heart surgery for patient, or even death.

In the prior art, if mispositioning of the support frame is found during release, the operator may hold the core shaft and push the sheath, i.e. withdraw the core shaft relatively, to force the support frame to enter into the sheath and be folded therein under the pressing of inner wall of the sheath until the support frame is completely surrounded by the sheath and returns to the state before release, then reposition and release the support frame. In view of this, by means of the relative movement between the sheath and the core shaft, positioning of the prosthesis valve can be adjusted when the support frame is positioned unsuccessfully. However, the aforementioned method is not only difficult to operate, but also has a low success rate. In particular, in the process of withdrawing the core shaft, due to the limited covering force provided by the sheath, and the insufficient constraint force provided by the sheath, there is a risk that the latching members at the end of the support frame may exit from the groove on the peripheral of a fixing head of the sheath core. However, on the other hand, increasing the strength of the sheath will reduce the compliance of the sheath which results in inconvenience for the interventional operation.

SUMMARY

The invention provides a delivery system facilitating retrieval and repositioning of an interventional device. The delivery system may be used to carry out interventional operations at the heart or vessels, and enables the interventional device to be held tightly and retrieved by further surrounding the sheath with an axially movable tube, and prevents the interventional device from falling out, thereby reducing the risks of surgery risks, thus the risk of mortality.

A delivery system facilitating retrieving the interventional device comprises a sheath and an operation handle for driving the sheath to move. The sheath comprises a carrier section at a proximal end used for surrounding the interventional device and a pusher section connected with the carrier section. A tube is provided which surrounds an outer periphery of the sheath and is slidably engaged with the sheath in an axial direction, wherein depending on different axial positions relative to the sheath, the tube can assume an initial configuration in which a proximal end portion of the tube is located at an outer periphery of the pusher section and an operation configuration in which the proximal end portion of the tube is held tightly around the carrier section, and wherein the tube in the operation configuration limits further expansion of the carrier section.

In the delivery system according to the present invention, the end adjacent to a lesion site is defined as the proximal end, and the other end distant from the lesion site (i.e. the end closer to an operator) is defined as the distal end.

The proximal end of the sheath has an expanded profile when carrying an interventional device, or the sheath is provided with a carrier section for carrying the interventional device. The carrier section for receiving a support frame in a compressed profile generally has a larger diameter than the other section of the sheath (referred to as the pusher section). The proximal end portion of the tube moves axially from the initial configuration until it is held tightly around the carrier section, i.e., transforming into the operation configuration, by means of axial movement of the tube.

In the delivery system according to the present invention, a core shaft is provided in the sheath, and the operation handle is used to drive the sheath to move relative to the core shaft. During the implantation procedure, if it is found that the interventional device is not completely released, yet is placed incorrectly, or the interventional device has been released completely at an incorrect position, the interventional device can be withdrawn and at least a partial portion thereof can reenter into the carrier section. Then the tube is pushed axially towards the carrier section, and the tube gradually surrounds the carrier section, and finally the sheath is pushed (in the mean time, the interventional device is withdrawn in a relative manner) such that the interventional device is gradually retrieved back into the carrier section of the sheath. The support frame is gradually folded under the pressing of the inner wall of the sheath until being completely surrounded by the carrier section of the sheath and returning to the profile before being released, and the retrieval of the support frame is achieved.

According to the invention, by surrounding the carrier section of the sheath with the tube (mainly the proximal end portion), on one hand the overall strength and the anti-expansion performance of the carrier section are increased, and on the other hand the end of the interventional device is locked more firmly to prevent the interventional device from falling out.

The proximal end portion of the tube is fitted with the pusher section using an interference fit, a clearance fit, or a transition fit, in the initial configuration.

In the present invention, if deformation of the tube does not occur in different configurations, there would exist a gap between the proximal end portion of the tube and the pusher section in the initial configuration since the proximal end portion of the tube is required to surround the carrier section which has a larger diameter than the pusher section. Taking into account the difficulty of advancing the tube, the tube should have a diameter as small as possible before turning into the operation configuration.

It is preferred that the gap between the inner wall of the tube and the outer wall of the pusher section of the sheath is not more than 0.1 mm, in which the inner wall of the tube refers to the area where the tube has the minimum diameter.

It is preferred that the proximal end portion of the tube is an expandable constraint section, and the diameter thereof, increases when transforming into the operation configuration from the initial configuration.

Alternatively, the proximal end portion of the tube is a non-expandable constraint section, and the diameter thereof remains unchanged when transforming into the operation configuration from the initial configuration.

The expandable constraint section can be interpreted as an elastic section, with a diameter thereof changing in different configurations. The expandable constraint section can hold the sheath tightly in the operation configuration, while the expandable constraint section has a smaller diameter in the initial configuration which facilitates axial movement of the tube.

The objectives of the present invention can also be achieved by means of the non-expandable constraint section, though its diameter remains unchanged when transforming into the operation configuration from the initial configuration.

The tube moves axially to first surround the connecting portion between an end of the interventional device and the delivery system to secure the connecting portion and to prevent the interventional device from falling off. The tight fit between the tube in the operation configuration and the carrier section will minimize the space for allowing the carrier section to deform, and improve the plasticity and toughness of the carrier section which are required for receiving the expanded interventional device. Furthermore, the tight fit therebetween also reduces the maximum outer diameter of the expandable constraint section and improves the compliance of the expandable constraint section in the initial configuration, and thus facilitates carrying out the interventional operation.

It is preferred that the proximal end portion of the tube (the portion which surrounds the outer periphery of the carrier section in the operation configuration) has an axial length which is at least 0.2 times of an axial length of the carrier section.

It is preferred that the proximal end portion of the tube has an axial length which is at least 1 time of an axial length of the carrier section.

It is preferred that the proximal end portion of the tube has an axial length which is at least 0.5 times to 2 times of an axial length of the carrier section.

In order to ensure the constraint effect, the proximal end portion of the tube surrounds at least about half of the carrier section in its axial length. For example, in the case that the proximal end portion of the tube has an axial length which is 1 time of an axial length of the carrier section, when the proximal end portion of the tube is in the operation configuration, the proximal end of the tube is substantially flush with a proximal end of the carrier section.

It is preferred that at least one of the tube and the sheath has a smooth contact surface at the contact portion therebetween, further preferably, both of the tube and the sheath have smooth contact surfaces at the contact portion. Although the smooth contact surface is not necessarily a precise standard continuous arcuate surface, it should at least not obstruct axial movement of the tube and/or the sheath.

Preferably, to facilitate operation or drawing of the tube, the tube extends to a distal end of the sheath as an integral structure.

In the case of a non-integral structure, the proximal end portion of the tube may be welded or bonded with the remaining portion of the tube. The material and the shape of the distal end portion of the tube are not limited since the tube mainly constrains the carrier section of the sheath by means of the proximal end portion thereof, while the distal end portion of the tube does not contact the carrier section of the sheath. In the case of extending as an integral structure that is made in one piece, the tube has constant cross section in configuration.

It is preferred that the outer periphery of the expandable constraint section is provided with a constraint sleeve.

The constraint sleeve may be made of a radially expandable elastic material or a non-elastic material with limited size in the radial direction.

It is preferred that the constraint sleeve is made of an elastic material and tightly surrounds the outer periphery of the expandable constraint section.

The constraint sleeve can prevent the tube from expanding and has the advantages of retaining the tube in the initial configuration in a smaller profile when the proximal end portion of, or the whole of, the tube is an expandable holding structure.

The constraint sleeve preferably extends axially beyond a proximal end of the expandable constraint section, and the portion of the constraint sleeve exceeding the expandable constraint section has a shrunken structure.

It is preferred that the constraint sleeve is provided with tear lines, and the constraint sleeve is torn at the tear lines under the expansion of a folded structure in the operation configuration.

It is preferred that the constraint sleeve is divided into several regions by the tear lines and at least a part of each region is fixed to the outer wall of the expandable constraint section, such as by adhesive, to prevent the constraint sleeve from falling off after the constraint sleeve is torn which might result in operation risks.

With regard to the tube, the invention provides the expandable constraint section as the preferred structure.

The expandable constraint section may be made of an elastic material, or preferably has a folded structure which is radially expandable and has an enclosed tubular shape in an expanded state.

The tube with the folded structure is made of a non-elastic material which is able to control a maximum size of expansion, otherwise, the constraint force of a tube which is elastically deformable applied to the carrier section of the sheath may be relatively weak, and there is always a possibility for allowing the tube to deform and expand further.

Preferably, the folded structure has at least one folded portion arranged in a circumferential direction of the tube.

Preferably, the folded structure has one to six folded portions arranged in sequence in the circumferential direction of the tube.

Preferably, the bending portion of the folded structure is provided with a crease line, and the crease line may be processed by means of thermoforming, and thus, the bending portion in the initial configuration is flattened.

The tube with the folded structure may be made of PTFE or the like, and the wall thickness of the tube is 0.1 mm to 1 mm, preferably 0.25 mm to 0.5 mm.

The folded structure may extend circumferentially in a wave manner or zigzag manner, which allows the expandable constraint section to deform more flexibly in its section. However, the radial compliance of the expandable constraint section should also be taken into consideration when other manners are adopted.

Due to the folded structure, folds or undulations are formed on the outer wall of the folded structure which may affect the surface smoothness and may be adverse to its delivery in the body. As such, by using the constraint sleeve, the folds or undulations can be covered, and the smoothness of the portions in contact with the body, and thus the safety can be improved.

Preferably, the non-expandable constraint section is a spiral structure, and coils of the spiral structure are axially arranged and abut against one another.

The spiral structure functions to provide a required axial pushing force. For further profiling the spiral structure, preferably, a holding sleeve is provided around an outer periphery of the spiral structure, and/or a lining is provided at an inner wall of the spiral structure.

An end portion of the non-expandable constraint section preferably forms an elastic shrunken section.

In order to drive the constraint sleeve to slide axially, preferably, the distal end of the constraint sleeve is fixed with the tube. Alternatively, the distal end of the constraint sleeve is operative with the operation handle and moves axially and simultaneously with the tube.

It is yet preferred that, the expandable constraint section of the tube comprises a tubular wall which is a coiled structure and has a coil-shaped cross section. The tubular wall is made of a flexible material which allows the tubular wall to automatically transform between the operation configuration and the initial configuration.

The operation configuration and the initial configuration of the tubular wall correspond to the operation configuration and the initial configuration of the tube. In the invention, the initial configuration only refers to a state at a specific position rather than a state defined by the operation procedure or the operation time. In the present invention, the initial configuration is a state before the tubular wall reaches the carrier section, or a state in which the tubular wall is withdrawn and separated from the carrier section after the external force is removed.

The tubular wall is a coiled structure extending in a circumferential direction and has an initial configuration. Thus, it should be understood that the material exhibits a degree of elasticity or at least has deformability, and functions to return to the initial configuration under no force after the external force is removed.

In operation, the tubular wall expands only when sliding to the carrier section of the sheath, and once the tubular wall is withdrawn from the carrier section, the coiled structure returns to its initial configuration. In view of this, the tube is allowed to be inserted into a thin-profile blood vessel in its initial configuration and is enlarged partially only when in action, which minimizes the expansionary deformation of the blood vessel and stimulation to the blood vessel.

The tubular wall is made of an elastic material, such as HDPE or Pebax or the like, which allows the tubular wall to flexibly transform between the operation configuration and the initial configuration. In order to ensure that the tubular wall is able to return to its initial configuration after the external force is removed, and retain certain strength and compliance, the thickness of the tubular wall is preferably 0.2 mm to 0.5 mm.

In order to surround the sheath, the tubular wall in the initial configuration is preferably coiled circumferentially more than one circle, and the exceeding portion extending beyond 360 degrees overlaps with a partial portion within 360 degrees, which prevents the sheath inside from being exposed.

Although the expandable constraint section is partially overlapped in a circumferential direction, it is not enclosed, that is why the coiled structure is expandable. The larger the coil angle of the tubular wall (i.e. the central angle corresponding to the start and end of the tubular wall), the larger the deformation degree allowed by the tubular wall. However, excessively coiling may result in negative effects such as a large resistance for expansion. Specific angles may depend on the variation in diameter in two configurations, with the tubular wall requiring sufficient circumference to enclose a channel for the interventional device.

Preferably, the coil angle of the tubular wall in the initial configuration is not more than 720 degrees.

Because the tubular wall is made of an elastic material, it is preferred to use the tubular wall in combination with a constraint sleeve made of a non-elastic material, to control the maximum size of radial expansion of the tubular wall.

In order to operate the tube to slide axially relative to the sheath, the invention provides a driving mechanism at the distal end of the sheath for driving the tube to move axially.

Optionally, the driving mechanism comprises:

a sliding member fixed to the tube; and a positioning means operating between the sliding member and the sheath or between the sliding member and the operation handle.

Optionally, the positioning means is a positioning member fixed to the sheath or the operation handle. The positioning member and the sliding member are provided with snap-fit structures engaged with each other. Alternatively, the positioning member is engaged with the sliding member in a plug-in manner or a threaded manner.

The positioning of the tube is achieved by means of the engagement between the positioning member and the sliding member.

Preferably, the sliding member is slidably mounted around the sheath.

The positioning means preferably includes a nut cap and a spring washer which are both mounted around the sheath, wherein the sliding member is threadably engaged with the nut cap, and the spring washer is pressed between the sliding member and the nut cap and holds the sheath tightly in a pressed state.

Preferably, the sliding member is provided with an annular groove, and the spring washer is arranged in the annular groove.

Optionally, the driving mechanism comprises:

a sliding member fixed to the tube; and a motor or a driving handle wheel arranged on the operation handle and engaged with the sliding member in a transmission manner.

The tube can be driven and positioned more conveniently by using a motor. It is also possible for the tube to be driven manually, i.e., using the driving handle wheel to transform the rotary motion to a linear motion of the tube, which is convenient to control.

In the case of using a motor for driving, optionally, a lead screw is connected to a driving shaft of the motor, and a sliding block is fixedly connected to the sliding member and threadably engaged with the lead screw.

In the case of using a motor for driving, optionally, a driving gear is provided on a driving shaft of the motor, and the sliding member has a rack engaged with the driving gear.

In the case of manual driving, the rotation axis of the driving handle wheel is parallel or perpendicular to the axis of the tube.

Optionally, a driving handle wheel is axially connected to a housing of the operation handle, the driving handle wheel is provided with a gear coaxially fixed thereon, and the sliding member is connected with a rack which is engaged with the gear.

Optionally, a driving handle wheel is axially connected to a housing of the operation handle, a lead screw is coaxially fixed to the driving handle wheel, and the lead screw is threadably engaged with a sliding block. The sliding block is fixedly connected to the sliding member.

Optionally, a driving handle wheel is axially connected to a housing of the operation handle, the housing of the operation handle is further axially connected with a pressing wheel which engages with the driving handle wheel, and the sliding member is arranged between the driving handle wheel and the pressing wheel.

The delivery system facilitating retrieval and repositioning of the support frame according to the present invention solves the problem of retrieval of a valve which has been deployed at an improper position. The delivery system functions to hold the support frame tightly by surrounding the sheath with the axially movable tube, retrieving the support frame and preventing the support frame from falling off from the core shaft, thereby reducing potential risks in surgery and thus the mortality rate. In addition, the tube may be driven manually or by other means, which is convenient to coordinate with known control handles or sheaths.

BRIEF DESCRIPTION OF THE DRAWINGS

FIG. 1 is a structural schematic view of a delivery system according to the present invention.

FIG. 2 is a sectional view of a carrier section of a sheath of the delivery system according to the present invention.

FIG. 3 is a schematic view of a tube in an operation configuration.

FIG. 12a is a schematic view of a proximal end of a tube as a non-expandable constraint section.

FIG. 12b is a schematic view of the non-expandable constraint section of FIG. 12a in an operation configuration.

DESCRIPTION OF THE EMBODIMENTS

Embodiment I

Figure 4:
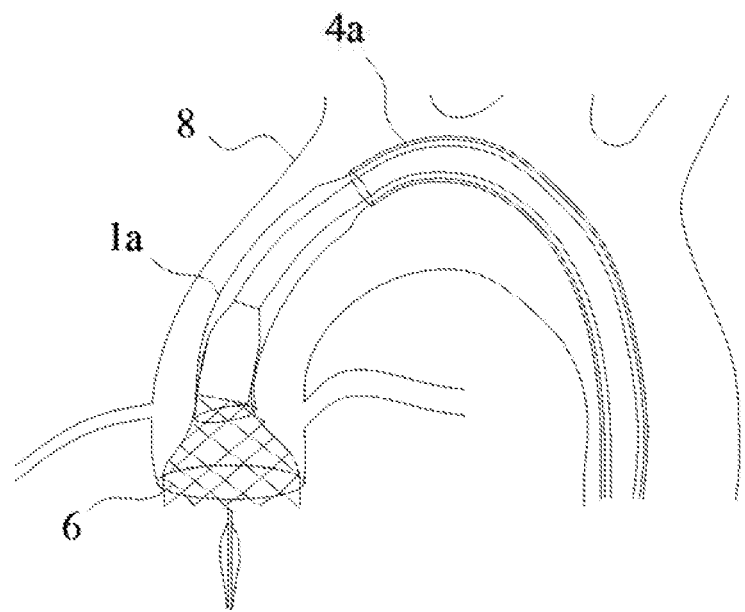
FIG. 4 is a schematic view of the delivery system according to the present invention in an operation configuration in a human body.

Referring to FIGS. 1 to 3, a delivery system according to the present invention includes a sheath 1, a core shaft 2 arranged in the sheath 1, and an operation handle 3. The core shaft 2 includes a core tube 2a, a support frame fixing head 2b, an installation section 2c and a guiding head 2d, which are connected in sequence from a distal end to a proximal end. During implantation of a valve, a support frame carrying a prosthesis valve is engaged into the clamp slots 2e on the support frame fixing head 2b by means of a latching means at the end of the support frame. Then, the sheath 1 is mounted around the core shaft 2 and forces the support frame to maintain a compressed profile. The sheath 1 and the core shaft 2 carrying the support frame are pushed from an entrance of a blood vessel to a lesion site. Then, the sheath 1 is withdrawn by means of operating a control button 7 on the operation handle 3 to release the support frame which then expands and positions itself in place at body temperature, and then the sheath 1 and the core shaft 2 are withdrawn.

The sheath 1 has a carrier section 1a at a proximal end thereof for surrounding the support frame, and a pusher section 1b connected with a distal end of the carrier section 1a. The pusher section 1b is surrounded by a tube 4 that is slidably engaged in an axial direction. A proximal end of the tube 4 has an expandable constraint section 4a which has an operation configuration in which the expandable constraint section 4a is held tightly around the carrier section 1a, and an initial configuration in which the expandable constraint section 4a is located at an outer periphery of the pusher section.

The diameter of the expandable constraint section 4a shown in the figures increases from the initial configuration to the operation configuration, and thus, the expandable constraint section 4a has a smaller diameter in the initial configuration.

In another embodiment according to the present invention, a proximal end of the tube 4 can be a non-expandable constraint section, i.e., the diameter of the proximal end of the tube 4 remains the same from the initial configuration to the operation configuration, which has the advantages of simpler manufacturing and a simpler structure, while constraining the carrier section in the operation configuration.

In the delivery system according to the present invention, the end adjacent to a lesion site is defined as the proximal end, and the other end distant from the lesion site is defined as the distal end. The carrier section 1a at the proximal end of the sheath has a larger diameter than the pusher section 1b since the carrier section 1a is required to receive the support frame in the compressed profile. As the expandable constraint section 4a moves to the proximal end, the expandable constraint section 4a expands and deforms radially from the initial configuration to surround and constrain the carrier section 1a until completely transforming into the operation configuration. It can be understood that the length for which the expandable constraint section 4a surrounds the carrier section 1a can vary depending on the clinical requirements for the operation.

In order to achieve axial movement of the tube relative to the sheath, a driving mechanism 5 for driving the tube 4 to move axially is provided at the distal end of the sheath 1.

Referring to FIG. 4, taking aortic valve replacement operation for example, during the procedure, the sheath and the core shaft carrying the support frame 6 are pushed from an entrance of a femoral artery to a lesion site through the aortic arch 8. The sheath is then withdrawn by means of the operation handle, and the support frame 6 is gradually exposed from the carrier section 1a and expands at body temperature.

Referring to FIG. 3, if the support frame 6 is found to have been released at an improper position, the tube can be first pushed axially towards the lesion site, and when the expandable constraint section 4a of the tube reaches the carrier section 1a, the expandable constraint section 4a deforms and expands to gradually surround the carrier section 1a, which on one hand increases the overall strength and the anti-expansion performance of the carrier section 1a, and on the other hand, restricts the latching members at the end of the support frame 6 in the clamp slots on the support frame fixing head to prevent the support frame from falling out.

The sheath is further pushed forward after the carrier section 1a is completely surrounded by the expandable constraint section 4a, and the expandable constraint section 4a and the carrier section 1a move together and synchronously towards the proximal end, i.e. the support frame is withdrawn, such that the support frame 6 is gradually retrieved back into the carrier section 1a of the sheath again. The support frame 6 is gradually folded under the pressing action of the inner wall of the carrier section 1a until being completely surrounded by the carrier section 1a and returning to the profile before being released, so that the retrieval of the support frame 6 is achieved.

In order to constrain the carrier section 1a, the expandable constraint section 4a in the operation configuration is tightly fitted with the outer wall of the carrier section 1a to prevent further expansion of the carrier section 1a when the support frame deforms. The tight fit between the expandable constraint section 4a and the carrier section 1a also reduces the maximum diameter of the expandable constraint section 4a and improves the compliance of the expandable constraint section 4a in the initial configuration, thereby facilitating the implementation of the interventional operation.

In the present embodiment, the expandable constraint section 4a has an axial length which is 1.2 times of the axial length of the carrier section 1a, and the carrier section 1a can be completely surrounded as desired. The proximal end of the expandable constraint section 4a in the operation configuration is substantially flush with the proximal end of the carrier section 1a.

The expandable constraint section 4a at its distal end may extend to the distal end of the sheath with an integral structure that is formed in one piece, or with a non-expandable constraint section structure.

In the case of a non-expandable constraint section structure, the non-expandable constraint section structure is tube-like and slidably mounted around the non-carrier section of the sheath. The tube in the initial configuration is adjacent to the outer wall of the pusher section i.e., the non-expansion section of the sheath, for example, with a gap therebetween of not more than 0.1 mm. The expandable constraint section 4a in the initial configuration may have an inner diameter which is the same as the inner diameter of the remaining portion of the tube, and the tube should have a small size to improve the compliance thereof.

In the present embodiment, the remaining portion of the tube, except the expandable constraint section, is made of PTFE or the like, and the material of the expandable constraint section 4a is selected from HDPE or Pebax or the like, and the wall thickness thereof is 0.5 mm.

Embodiment II

Figure 5:
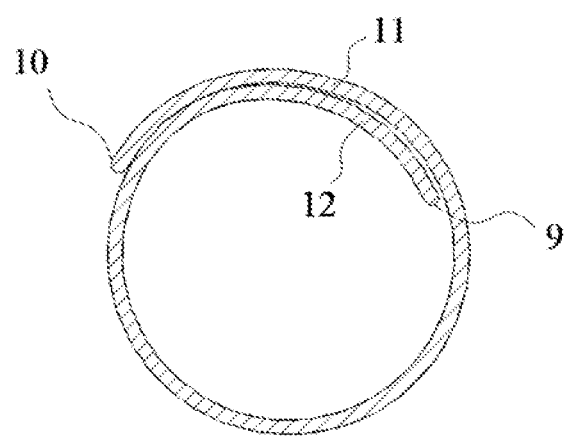
FIG. 5 is a sectional view of an expandable constraint section of a tube of the delivery system according to the present invention in an initial configuration.

A delivery system according to a second embodiment differs from that of the first embodiment in that the expandable constraint section of the tube 4 is a coiled structure in the second embodiment, with the remaining parts being the same as those of the first embodiment. Referring to FIG. 5, the expandable constraint section in the present embodiment includes a tubular wall which is a coiled structure. A coil angle of the tubular wall is more than 360 degrees such that the expandable constraint section in an initial configuration can surround the sheath, that is, the coiled structure runs circumferentially more than 360 degrees from the starting end 9 to the terminal end 10, wherein an exceeding portion extending beyond 360 degrees overlaps with a partial portion within 360 degrees.

As shown in the figure, the exceeding portion 11 and the non-exceeding portion 12 are overlapped with each other, and the exceeding portion 11 covers the outer periphery of the non-exceeding portion 12, as a result, a circumferentially enclosed channel is formed in the interior of the tubular wall.

Figure 6:
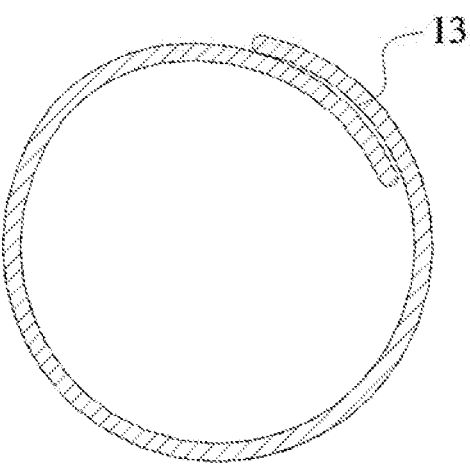
FIG. 6 is a sectional view of the expandable constraint section of FIG. 5 in an expanded state.

Referring to FIG. 6, the expandable constraint section surrounding the carrier section of the sheath is expanded, the coil angle of the tubular wall in an operation configuration is also not less than 360 degrees (that is, there still exists an overlapping portion 13) to avoid exposure of the carrier section.

Figure 7:
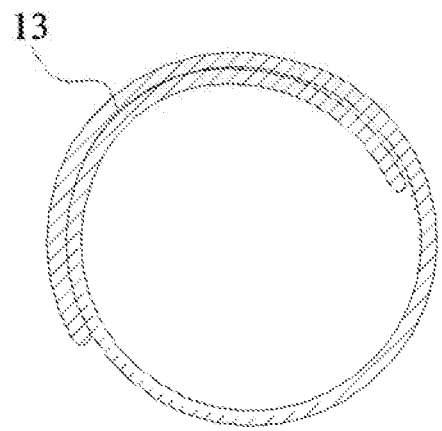
FIG. 7 is a sectional view of an expandable constraint section with a different coil angle.

FIG. 7 shows an enlarged overlapping portion 13, in which the coil angle of the tubular wall is increased to 540 degrees, and thus the tubular wall has a larger inner diameter after being expanded, which allows a carrier section with a larger diameter to pass through.

Figure 9:
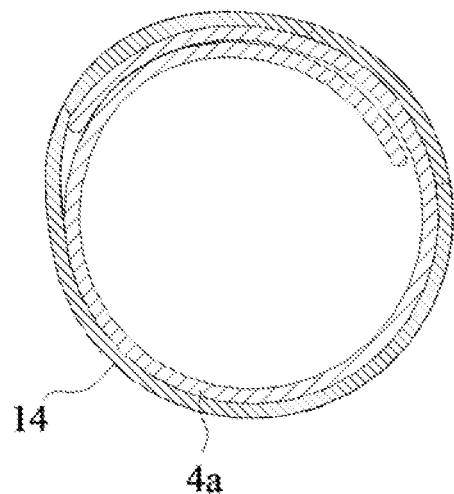
FIG. 9 is a sectional view showing an expandable constraint section of a coiled structure accommodated in a constraint sleeve.

Referring to FIG. 9, the expandable constraint section 4a of the tube is a coiled structure, and a constraint sleeve 14 is provided around an outer periphery of the tube.

Embodiment III

Figure 8A:
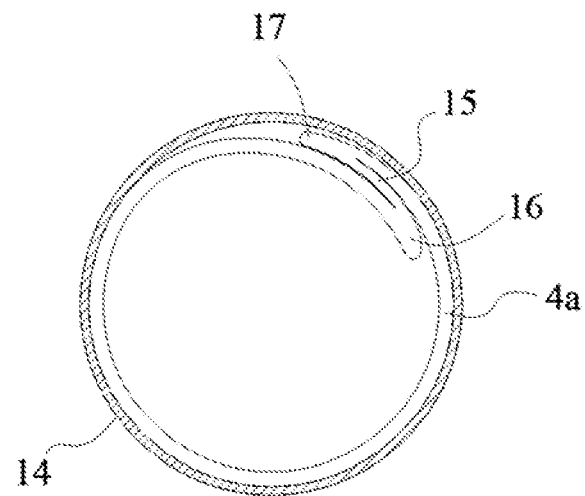
FIG. 8a is a sectional view of an expandable constraint section with a folded structure.

A delivery system according to a third embodiment differs from that of the first embodiment in having different expandable constraint sections in structure, with the remaining parts being the same as those of the first embodiment. Referring to FIG. 8a, another embodiment of the present invention is provided, in which the expandable constraint section 4a has a folded structure 15 which is provided with crease lines at bending portions 16, 17 thereof. The crease lines may be processed by means of thermoforming; thus, the bending portions in the initial configuration are flattened. The expandable constraint section 4a may be made of PTFE and have a wall thickness of 0.25 mm to 0.5 mm.

Figure 8B:
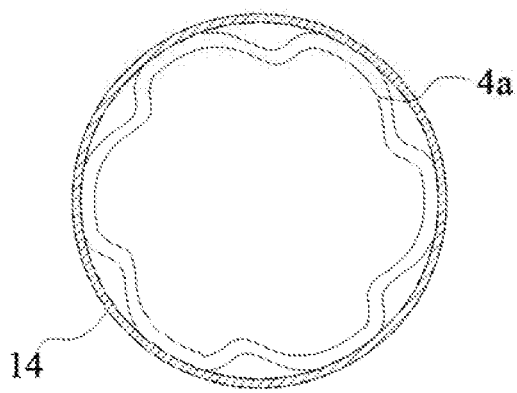
FIG. 8b is a sectional view of an expandable constraint section with another folded structure.

Referring to FIG. 8b, in another embodiment provided in the present invention, a folded structure of the expandable constraint section 4a is a structure with peaks and valleys arranged in a circumferential direction; in other words, the folded structure of the expandable constraint section 4a is wave shaped.

Figure 8C:
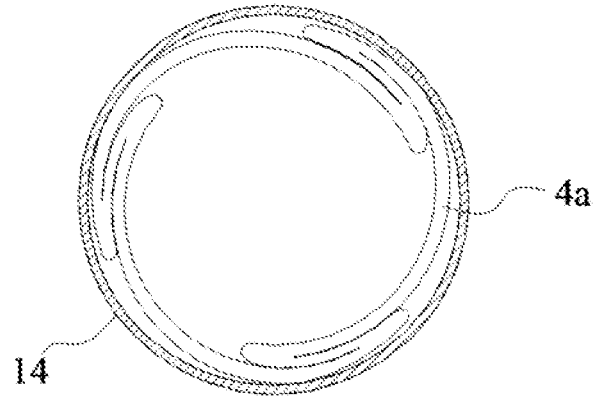
FIG. 8c is a sectional view of an expandable constraint section with a third folded structure.

Referring to FIG. 8c, in another embodiment according to the present invention, there are three folded portions in the expandable constraint section 4a.

In FIGS. 8a to 8c, each of the folded structures is in the form of an enclosed tube, which can provide sufficient constraint force in the radial direction to prevent the carrier section of the sheath from further expanding, and the interventional device from falling out.

Referring to FIGS. 8a to 8c and FIG. 10, a constraint sleeve 14 is provided around an outer periphery of the tube in another embodiment according to the present invention.

Figure 10:
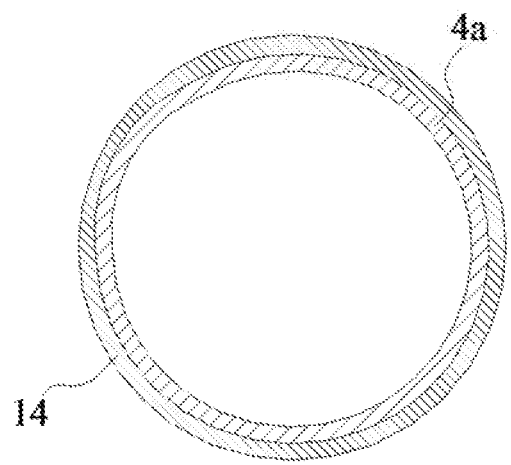
FIG. 10 is a sectional view of an expandable constraint section of a folded structure, with the folded structure deployed under expansion.

In the case of a folded structure, the constraint sleeve 14 which engages with the expandable constraint section 4a is made of an elastic material. Referring to FIG. 10, the constraint sleeve 14 expands as the folded structure expands into its operation configuration, while the constraint sleeve 14 in the initial configuration forces the folded structure to return to its initial configuration due to the elasticity thereof, thereby retaining the tube in a smaller diameter in whole.

In the case of a coiled structure, the constraint sleeve 14 which engages with the expandable constraint section 4a may be made of a non-elastic material to limit the maximum expansion. The constraint sleeve is folded or pleated or the like in the initial configuration, and is expanded radially in the operation configuration. However, after being expanded to a certain extent, the constraint sleeve 14 will not be able to deform anymore owing to low elasticity thereof, so that it can hold the carrier section tightly.

Embodiment IV

Figure 11A:
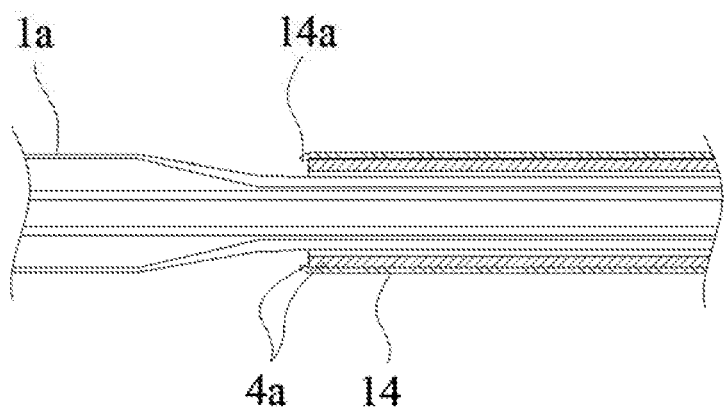
FIG. 11a is a sectional view of an end portion of a constraint sleeve.

Referring to FIG. 11a, in a fourth embodiment according to the present invention, a constraint sleeve 14 axially extends beyond the proximal end of the expandable constraint section 4a, and the portion of the constraint sleeve 14 exceeding the expandable constraint section 4a has a shrunken structure 14a for facilitating axial push.

Figure 11B:
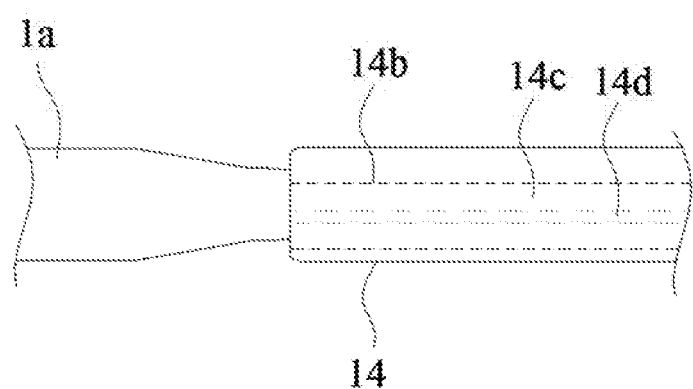
FIG. 11b is a structural schematic view of an end portion of a constraint sleeve with a tear line.

Referring to FIG. 11b, the constraint sleeve 14 is further provided with a tear line 14b. In the operation configuration, the folded structure is expanded and accordingly the constraint sleeve 14 is torn at the tear line 14b. The constraint sleeve 14 may be provided with a plurality of tear lines 14b which axially extend over the constraint sleeve 14. The tear lines 14b may be straight or curved. The entire constraint sleeve 14 is divided into several regions by the tear lines 14b, wherein at least a part of each region is fixed to the outer wall of the expandable constraint section 4a by adhesive. For example, one of the regions 14c is fixed to the outer wall of the expandable constraint section 4a by means of an adhesive region 14d.

Figure 11C:
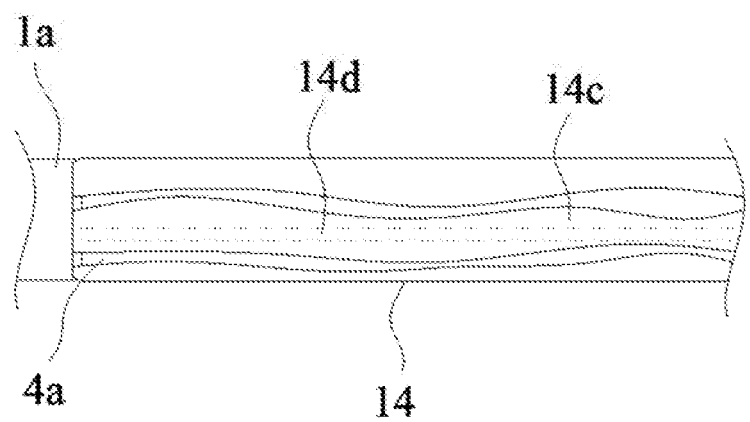
FIG. 11c is a structural schematic view of the constraint sleeve after having been torn.

Referring to FIG. 11c, when the constraint sleeve 14 moves with the expandable constraint section 4a to the carrier section 1a, the constraint sleeve 14 is torn at the tear lines 14b with the expansion of the expandable constraint section 4a. As a result, the expandable constraint section 4a is visible from the torn portions. The region 14c will not fall off from the expandable constraint section 4a because the region 14c is fixed to the expandable constraint section 4a by means of the adhesive region 14d, such that the regions 14c can be retrieved and prevented from being left in the body.

Embodiment V

Referring to FIG. 12a, in a fifth embodiment according to the present invention, the proximal end of the tube is a non-expandable constraint section 4b in a straight tubular shape. Referring to FIG. 12b, the diameter of the non-expandable constraint section 4b remains substantially unchanged during movement to the carrier section 1a from the initial configuration to the operation configuration. The non-expandable constraint section 4b can provide a greater radial constraint force to hold the carrier section tightly and prevent it from further expanding.

Embodiment VI

Figure 13:
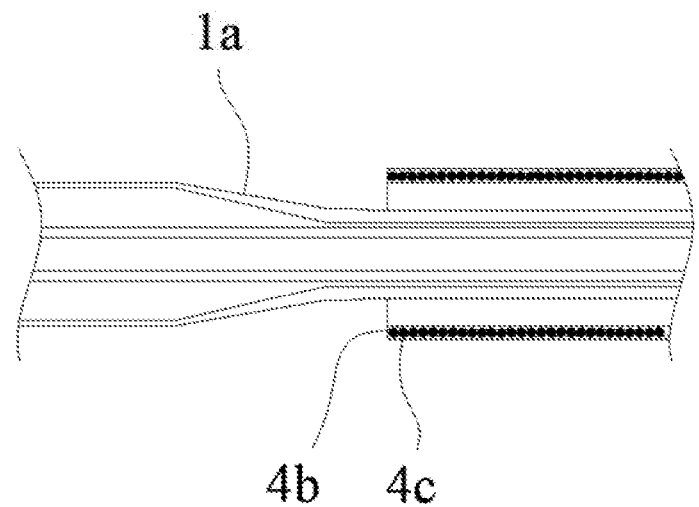
FIG. 13 is a schematic view of a non-expandable constraint section as a spiral structure.

Referring to FIG. 13, in a sixth embodiment according to the present invention, the proximal end of the tube is a non-expandable constraint section 4b, which has a spiral structure. Coils of the spiral structure are axially arranged and abut against one another. A holding sleeve is provided on an outer periphery of the spiral structure, and a lining is provided at an inner wall of the spiral structure. The spiral structure may be made of a flexible metal wire which is arranged between and sandwiched by the holding sleeve and the lining.

Embodiment VII

Figure 14A:
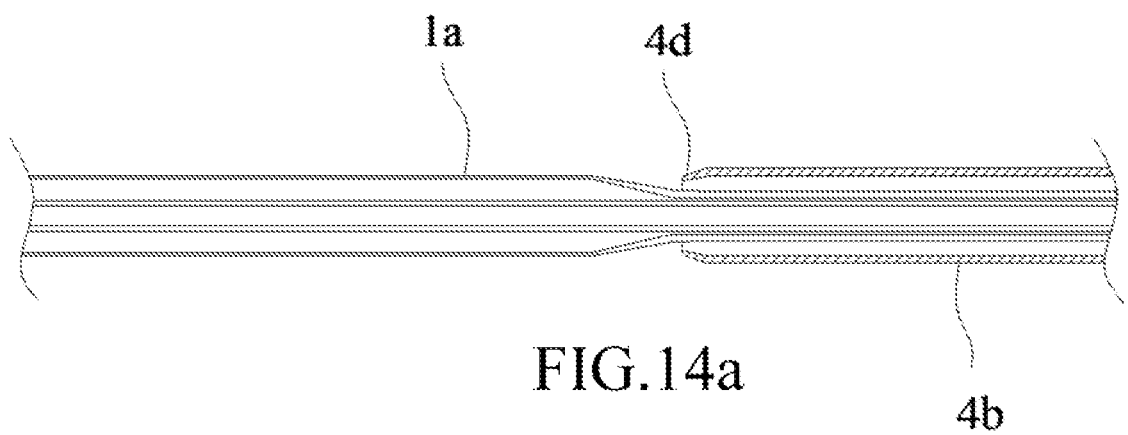
FIG. 14a is a schematic view of a non-expandable constraint section with a shrunken section.
Figure 14B:
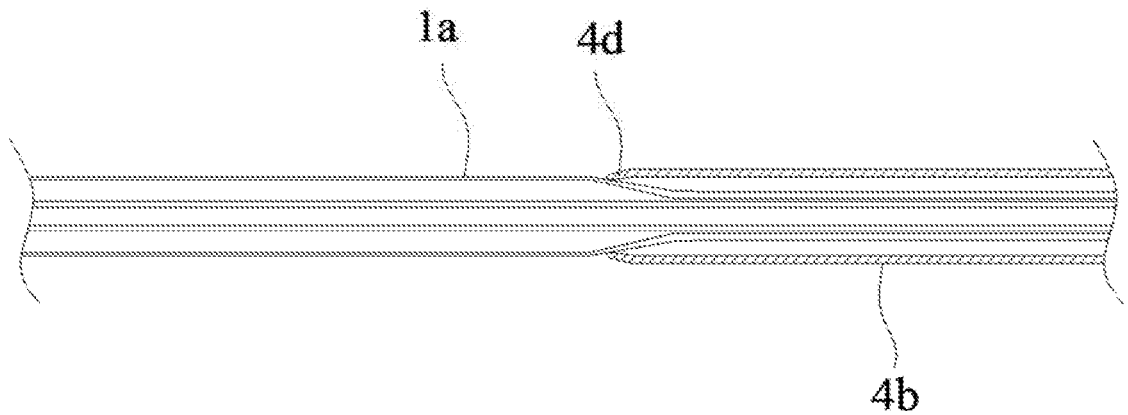
FIG. 14b shows a schematic view of the shrunken section of FIG. 14a as it begins to expand.

Referring to FIGS. 14a and 14b, in a seventh embodiment according to the present invention, an elastic shrunken section 4d is formed at the end of the non-expandable constraint section 4b for facilitating axial movement of the non-expandable constraint section 4b.

The shrunken section 4d is made of an elastic material and will expand if it abuts against the carrier section 1a, and gradually lead the entire non-expandable constraint section 4b into the operation configuration in which the non-expandable constraint section 4b surrounds the carrier section 1a.

Embodiment VIII

Figure 15:
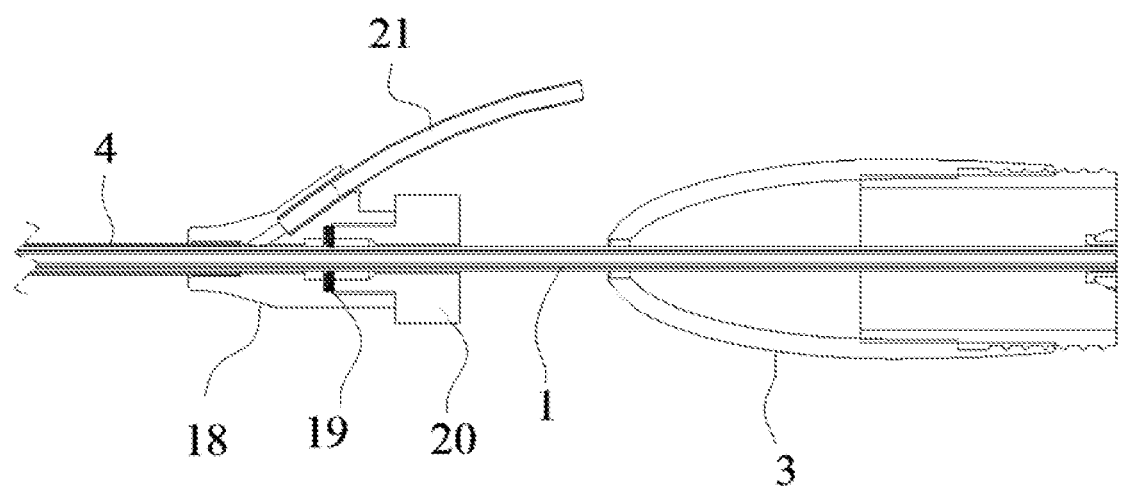
FIG. 15 is a structural schematic view of a driving mechanism for a tube of the delivery system according to the present invention.

Referring to FIG. 15, in an eighth embodiment, a driving mechanism is provided at the distal end of the sheath 1 to drive the tube 4 to slide axially relative to the sheath 1.

The driving mechanism includes a sliding member 18 fixed to the tube 4 and a positioning means operating between the sliding member 18 and the sheath 1.

The positioning means in the present embodiment includes a nut cap 20 and a spring washer 19 which are both mounted around the sheath 1. The sliding member 18 is slidably mounted around the sheath 1 and threadably engaged with the nut cap 20. The spring washer 19 is arranged in an annular groove which is provided in the sliding member 18, and is pressed between the sliding member 18 and the nut cap 20. The spring washer 19 holds the sheath 1 tightly in a pressed state, so as to fix the sliding member 18 and the nut cap 20 together with the tube 4 relative to the sheath 1 without axial movement.

The sliding member 18 is further connected with a branch tubing 21 through which water or other liquid can be injected into the gap between the tube 4 and the sheath 1 to eliminate air before operation.

When the tube 4 is required to slide, the nut cap 20 is rotated anticlockwise to release the spring washer 19, and thus the sliding member 18 can drive the tube 4 to slide axially. After the tube 4 has been positioned in place, the nut cap 20 is rotated clockwise to press the spring washer 19 against the sliding member 18 and the nut cap 20; as a result, the spring washer 19 deforms to hold the sheath 1 tightly so as to achieve proper positioning. A motor or a driving handle wheel may be provided on the operation handle 3 and be engaged with the sliding member in a transmission manner for facilitating the operation.

In the case of using a motor for driving, a lead screw is connected to a driving shaft of the motor. Further, a sliding block which is fixedly connected to the sliding member 18 is threadably engaged with the lead screw. Alternatively, a driving gear can be provided on the driving shaft of the motor, and correspondingly the sliding member 18 has a rack engaged with the driving gear.

In the case of manual driving, a driving handle wheel is axially connected to the operation handle 3. The driving handle wheel is provided with a gear coaxially fixed thereon. The sliding member 18 is connected with a rack engaged with the gear.

Alternatively, a driving handle wheel is axially connected to the operation handle 3, a lead screw is coaxially fixed on the driving handle wheel, and the lead screw is threadably engaged with a sliding block. The sliding block is fixedly connected to the sliding member 18.

Alternatively, a driving handle wheel is axially connected to the operation handle 3, and the operation handle 3 is further axially connected with a pressing wheel which engages with the driving handle wheel. A part of the sliding member 18 extends between the driving handle wheel and the pressing wheel. When the driving handle wheel and the pressing wheel rotate, the sliding member 18 is driven to move axially.

The positioning means may be a positioning member arranged on the operation handle 3. The positioning member and the sliding member are engaged with each other by means of snap-fit, plug-in or threaded connection.

Figure 16:
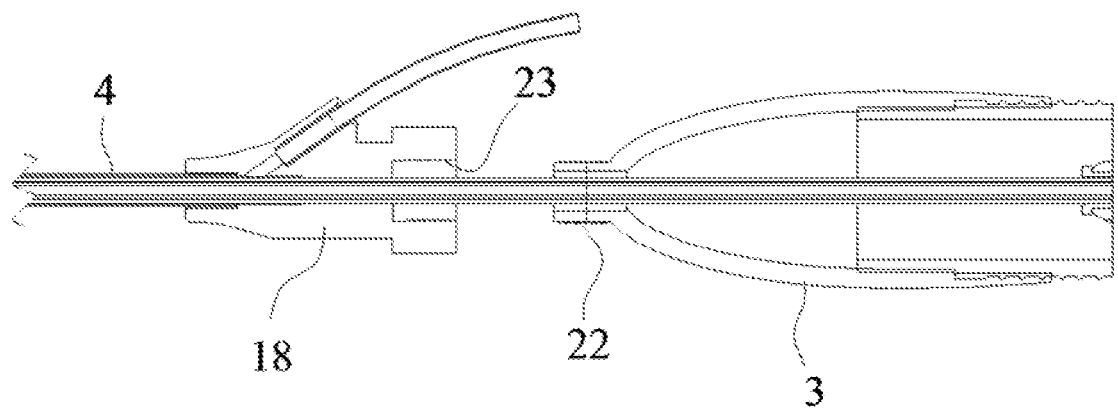
FIG. 16 is a structural schematic view of another driving mechanism for a tube of the delivery system according to the present invention.

Referring to FIG. 16, the positioning member provided on the operation handle 3 is an external threaded tube 22 integrally formed on the operation handle 3. The sliding member 18 is provided with inner thread 23 at an end facing the operation handle 3. The inner thread 23 is engagable with the external threaded tube 22. The sliding member 18 can be separated from the operation handle 3 by unscrewing, and then the tube 4 can be driven to move axially relative to the sheath.

The delivery system facilitating retrieval and repositioning of the support frame according to the present invention solves the problem of a retrieval valve which has been deployed at an improper position. The delivery system functions to hold the support frame tightly by surrounding the sheath with the axially movable tube, retrieving the support frame, and preventing the support frame from falling off from the core shaft, thereby reducing potential risks in surgery and thus the mortality rate. In addition, the tube may be manually driven or driven through other ways, which is convenient to coordinate with known control handles or sheaths.

What is claimed is:

1. A delivery system facilitating retrieval of an interventional device comprising:
    a sheath comprising a carrier section at a proximal end for surrounding the interventional device, and a pusher section connected with the carrier section;
    an operation handle for driving the sheath to move;
    a tube surrounding an outer periphery of the pusher section in slidable engagement connection, and
    a driving mechanism which comprises a sliding member fixed to the tube, a nut cap and a spring washer mounted around the sheath, wherein the sliding member is threadably engaged with the nut cap, the spring washer is pressed between the sliding member and the nut cap, and holds the sheath tightly in a pressed state;
    wherein depending on different axial positions, the tube assumes:
    an initial configuration in which a proximal end portion of the tube is located at the outer periphery of the pusher section; and
        an operation configuration in which the proximal end portion of the tube is held tightly around the carrier section, and the tube in the operation configuration limits further expansion of the carrier section;
        wherein the proximal end portion of the tube is:
        an expandable constraint section, and a diameter thereof increases when transforming into the operation configuration from the initial configuration; or
        a non-expandable constraint section, and a diameter thereof remains unchanged when transforming into the operation configuration from the initial configuration.

2. The delivery system facilitating retrieval of an interventional device according to claim 1, wherein the expandable constraint section comprises at least one folded structure which is expandable in a radial direction, and the tube is in a circumferentially enclosed tubular shape when the folded structure is at an expanded state.

3. The delivery system facilitating retrieval of an interventional device according to claim 2, wherein the folded structure extends in a zigzag manner and comprises at least three extension portions, and wherein the extension portions extend back and forth along a circumferential direction and abut against one another in the radial direction.

4. The delivery system facilitating retrieval of an interventional device according to claim 3, wherein the expandable constraint section comprises a plurality of folded structures which are arranged evenly along the circumferential direction; wherein each folded structure comprises a start end and a terminal end, with the start end of each folded structure connected with the terminal end of an adjacent folded structure, and the terminal end of each folded structure connected with the start end of an another adjacent folded structure.

5. The delivery system facilitating retrieval of an interventional device according to claim 2, wherein the folded structure is formed by protruding radially outwardly or being recessed radially inwardly, such that a cross section of the tube extends in a wave configuration.

6. The delivery system facilitating retrieval of interventional device according to claim 2, further comprising a constraint sleeve provided around an outer periphery of the expandable constraint section.

7. The delivery system facilitating retrieval of an interventional device according to claim 6, wherein the constraint sleeve is made of an elastic material, and tightly surrounds the outer periphery of the expandable constraint section.

8. The delivery system facilitating retrieval of an interventional device according to claim 6, wherein the constraint sleeve extends axially beyond a proximal end of the expandable constraint section, and the exceeding portion of the constraint sleeve beyond the proximal end of the expandable constraint section comprises a shrunken structure.

9. The delivery system facilitating retrieval of an interventional device according to claim 6, wherein the constraint sleeve is provided with tear lines.

10. The delivery system facilitating retrieval of an interventional device according to claim 9, wherein the constraint sleeve is divided into several regions by the tear lines, and at least a part of each region is fixed to an outer wall of the expandable constraint section.

11. The delivery system facilitating retrieval of an interventional device according to claim 1, wherein a cross section of the expandable constraint section of the tube is in a coiled shape, and the expandable constraint section has a start end and a terminal end overlapping each other in the radial direction without being connected with each other.

12. The delivery system facilitating retrieval of an interventional device according to claim 11, wherein the start end and the terminal end of the expandable constraint section are overlapped with each other in the radial direction when the tube assumes the operation configuration.

13. The delivery system facilitating retrieval of an interventional device according to claim 1, wherein the non-expandable constraint section is a spiral structure having a plurality of coils, and the coils of the spiral structure are axially arranged and abut against one another.

14. The delivery system facilitating retrieval of an interventional device according to claim 13, further comprising a holding sleeve provided around an outer periphery of the spiral structure.

15. The delivery system facilitating retrieval of an interventional device according to claim 13, further comprising a lining provided at an inner wall of the spiral structure.

16. The delivery system facilitating retrieval of an interventional device according to claim 1, further comprising an expandable shrunken section at an end portion of the non-expandable constraint section, wherein a diameter of the shrunken section is smaller than a diameter of the non-expandable constraint section, and an axial length of the shrunken section is smaller than an axial length of the non-expandable constraint section.

17. The delivery system facilitating retrieval of an interventional device according to claim 1, further comprising a driving mechanism which comprises a sliding member fixed to the tube, a rack fixed to the sliding member, and a gear engaged with the rack, wherein the gear is operated by the operation handle.

18. The delivery system facilitating retrieval of an interventional device according to claim 1, further comprising a driving mechanism which comprises a sliding block fixed to the tube, and a lead screw operated by the operation handle, wherein the lead screw is threadably engaged with the sliding block.

19. The delivery system facilitating retrieval of an interventional device according to claim 18, wherein the operation handle comprises a motor or a handle wheel, and the lead screw is driven by the motor or the handle wheel.

* * * * *